United States Patent [19]

Kitajima et al.

[11] 4,356,149
[45] Oct. 26, 1982

[54] MULTI-LAYER CHEMICAL ANALYTICAL MATERIALS

[75] Inventors: Masao Kitajima; Fuminori Arai; Asaji Kondo, all of Asaka, Japan

[73] Assignee: Fuji Photo Film Co., Ltd., Kanagawa, Japan

[21] Appl. No.: 165,444

[22] Filed: Jul. 2, 1980

[30] Foreign Application Priority Data

Jul. 2, 1979 [JP] Japan .................................. 54-83608

[51] Int. Cl.³ ...................... G01N 21/78; G01N 33/62
[52] U.S. Cl. ...................................... 422/56; 422/57; 435/12; 435/805
[58] Field of Search ................... 422/56, 57; 23/230 B; 435/805, 12

[56] References Cited

U.S. PATENT DOCUMENTS

| | | | |
|---|---|---|---|
| 3,011,874 | 12/1961 | Deutsch | 23/230 B X |
| 3,092,463 | 6/1963 | Adams, Jr. et al. | 422/56 |
| 3,212,855 | 10/1965 | Mast et al. | 422/56 |
| 4,089,747 | 5/1978 | Bruschi | 23/230 B X |

Primary Examiner—Arnold Turk
Attorney, Agent, or Firm—Sughrue, Mion, Zinn, Macpeak and Seas

[57] ABSTRACT

A multi-layer chemical analytical material comprising a support, a reagent layer on the support and a spreading layer on the reagent layer wherein the reagent layer is composed of a hydrophilic binder and fine hydrophobic particles dispersed in the hydrophilic binder, said hydrophobic particles containing a reagent capable of directly or indirectly reacting with the component being analyzed to produce a color change.

12 Claims, 2 Drawing Figures

MULTI-LAYER CHEMICAL ANALYTICAL MATERIALS

BACKGROUND OF THE INVENTION

1. Field of the Invention

This invention relates to an improved analytical material for use in the quantitative determination of a specific component contained in an aqueous liquid sample. More particularly, it is concerned with a multi-layer chemical analytical material comprising a support, a reagent layer and a spreading layer which is characterized in that the reagent layer is of an oil-in-water type dispersion wherein the reagent is contained in hydrophobic particles dispersed in a hydrophilic binder.

2. Description of the Prior Art

Multi-layer chemical analytical materials in sheet form which permit analysis by a dry operation are described, for example, in Japanese Patent Publication No. 33800/74 (corresponding to U.S. Pat. No. 3,630,957), Japanese Patent Application (OPI) Nos. 53888/74 (corresponding to U.S. Pat. No. 3,992,158), 137192/75 (corresponding to U.S. Pat. No. 3,983,005), 40191/76 (corresponding to U.S. Pat. No. 4,042,335), 3488/77 (corresponding to U.S. Pat. No. 4,006,403), 89796/78 (corresponding to U.S. Pat. No. 4,069,017), 131089/78 (corresponding to U.S. Pat. No. 4,144,306), etc. Those analytical materials are of the construction that a reagent layer of a single or multi-layer construction is provided on a support and an isotropically porous spreading layer is provided on the reagent layer. On dropping an aqueous liquid sample on the spreading layer, the aqueous liquid sample penetrates into the reagent layer and undergoes a color-forming reaction, and this change in color density permits determination of the concentration of a certain component in the aqueous liquid sample.

The quantitative determination of a certain component in an aqueous liquid can rarely be done with only one reagent and, consequently, a combination of several reagents is often used. For example, the quantitative determination of urea in blood is usually carried out not only by a direct determination using a single reagent but by a multi-stage reaction: urea is subjected to enzyme decomposition with a first reagent, urease, to form ammonia and the ammonia so formed is allowed to participate in the color formation by use of a second reagent, for example, a pH indicator or a mixed reagent of a diazonium salt and a coupler, whereby the quantitative determination of urea can finally be achieved.

In some of the multi-layer analytical sheets wherein a plurality of reagents are used for the multi-stage reaction, all of the reagents can be incorporated in the reagent layer of the single layer construction whereas for other multi-layer analytical sheets it is preferred that the reagents are divided into the first reagent and the second reagent according to the order of reaction and separately incorporated in a plurality of reagent layers.

The multi-layer analytical sheet as described in U.S. Pat. No. 3,011,874 and Japanese Patent Application (OPI) No. 3488/77 is of a complicated multi-layer construction wherein a reagent layer is divided into two layers, one of the layers being composed of a hydraulic binder and the other being composed of a hydrophilic binder or protected by a film of a hydrophobic substance so as to prevent water from penetrating therein. That is, the quantitative determination of a certain component in an aqueous liquid sample is carried out by reaction in water followed by reaction in a non-aqueous medium. For the production of such a multi-layer analytical sheet, there is generally employed a method wherein coating and drying are successively carried out and at least two coating-drying steps are required. Where the hydrophilic binder layer is provided directly on the hydrophobic layer, the adhesion between the two layers is weak and they often separate from each other in a short time. In the practice of this method, therefore, the hydrophobic binder layer is first provided, at least one additional adhesive layer called an undercoating layer or intermediate layer is then provided on the hydrophobic binder layer, and the hydrophilic binder layer is finally coated on the adhesive layer. Thus, the method wherein the reagent layer is divided into the hydrophobic and hydrophilic layers gives rise to the drawback that the production process is markedly complicated.

In accordance with the hitherto known methods for use in the quantitative determination of a certain component in an aqueous liquid sample wherein a plurality of reagents to be used are required to be divided into two or more groups, one group being reacted under hydrophilic circumstances and another group being reacted under non-aqueous circumstances, there has been employed a multi-layer analytical sheet of the complicated multi-layer construction in which the reagents are divided into a hydrophilic binder layer and the hydrophobic binder layer. On the other hand, the multi-layer analytical material of this invention is characterized in that the reagent layer is not divided into two layers and a single reagent layer composed of a hydrophilic binder and hydrophobic fine particles dispersed therein containing the reagent is employed.

A multi-layer analytical material containing therein a reagent layer prepared by dissolving in an organic solvent a hydrophobic reagent which is insoluble or sparingly soluble in water and which is soluble in an organic solvent, and dispersing in a hydrophilic binder polymer the organic solvent solution of the reagent as fine particles is described in Example 4 of Japanese Patent Application (OPI) No. 26188/78 (corresponding to U.S. Pat. No. 4,089,747) and in Japanese Patent Application (OPI) No. 73096/79 (corresponding to British Patent Publication No. 2 007 360A). However, in the reagent layer of such multi-layer analytical material, a complicated procedure is required for dispersing in the hydrophilic binder polymer the reagent which is insoluble or sparingly soluble in water such that the reagent which is insoluble or sparingly soluble in water is first dissolved in a solution of the organic solvent to prepare a mixed solution which is then dispersed as oily liquid fine particles. In contrast, in the multi-layer chemical analytical material of the present invention, fine particles containing the reagent functions not only to disperse in the hydrophilic binder polymer but also to prevent the permeation of water from the surface portion into the inside portion of the fine particles containing the reagent.

SUMMARY OF THE INVENTION

This invention provides:

A multi-layer chemical analytical material comprising a light-transmitting and water-impermeable support, a reagent layer on the support and an aqueous liquid sample-spreading layer on the reagent layer wherein the reagent layer is composed of a hydrophilic binder and fine hydrophobic particles dispersed in the hydrophilic binder, the particles containing a regent capable of undergoing a direct or indirect reaction with the component to be analyzed to produce a color change; and A multi-layer chemical analytical material as described above wherein the hydrophilic binder contains a second reagent capable of reacting with the component to be determined.

DETAILED DESCRIPTION OF THE INVENTION

Figure 1:
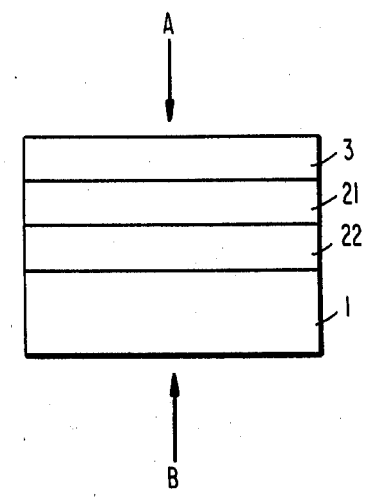
FIG. 1 is an illustrative cross sectional view of a conventional multi-layer analytical sheet.

One of the advantages of this invention is that the single layer construction of the reagent layer permits the coating step to be simplified to at least ½ that of the conventional multi-layer construction method as described previously.

Another advantage is that in the multi-layer chemical analytical material as described above, the apparent detection limit may be increased. The reason for this is considered that in the multi-layer analytical material of this invention including the single reagent layer in which the hydrophobic fine particles containing the reagent are dispersed, as apparent from the geometric structure, the distance between the reagent contained in the hydrophobic fine particle and the reagent present in the hydrophilic binder is short and the contact area between them is markedly enlarged in comparison with the conventional multi-layer analytical sheet provided with a plurality of reagent layers, which allows various reactions to proceed more smoothly until a color is formed.

Light-transmitting and water-impermeable supports for use in the multi-layer analytical material of this invention include plastic films such as polyethylene terephthalate, cellulose esters (e.g., cellulose diacetate, cellulose triacetate and cellulose acetate propionate), polycarbonate and polymethyl methacrylate, and glass plates; known transparent supports with a thickness of from about 50 μm to about 2 mm can be used.

Where the support is hydrophobic and the adhesion between the support and the hydrophilic binder of the reagent layer is insufficient, it may be subjected to processings to render the surface hydrophilic (e.g., ultraviolet ray irradiation, electron beam irradiation, flame processing, hydrolysis using alkali, etc.), or auxiliary processings, for example, the formation of an undercoating layer made up of a substance having appropriate adhesion to both the support and the hydrophilic binder of the reagent layer on the surface of the support and the formation of minute unevenness on the surface of the support to such an extent as not to greatly reduce the light transmission property (e.g., brushing and electrolytic etching).

The reagent which can be incorporated can be selected depending upon the nature of the component to be determined. However, those described in Japanese Patent Application (OPI) No. 3488/77 (corresponding to U.S. Pat. No. 4,066,403) are preferred as the reagent to be incorporated in the chemical analytical material of the present invention.

The hydrophobic fine particles of this invention are liquid or solid minute particles containing therein the reagent, which particles are permeable to a gas or a substance soluble in the hydrophobic solvent through diffusion or extraction, but not by water.

Such hydrophobic fine particles containing the reagent can be prepared by the same method as in Japanese Patent Application (OPI) No. 13320/74 (corresponding to U.S. Pat. No. 3,951,851) and exemplify oily minute particles prepared by adding a lipophilic binder polymer, tackifier, dye or pigment to oily matters prepared by dissolving the reagent in an organic solvent substantially incompatible with water; oily minute particles prepared by dissolving in an organic solvent substantially incompatible with water, a polymer soluble in an organic solvent, and dissolving or dispersing the reagent in the resulting solution; minute particles prepared by pulverizing a solid polymer containing the reagent; etc. In addition, those microcapsules prepared by encapsulating the above oily minute particles or minute particles prepared by pulverizing the solid polymer containing the reagent with a thin layer of a lipophilic polymer or a hydrophilic polymer can be used.

Organic solvents substantially incompatible with water which are used for the preparation of the minute particles as described above include liquid plasticizers such as phthalic acid esters (e.g., dimethyl phthalate, diethyl phthalate, dibutyl phthalate, dicyclohexyl phthalate and dioctyl phthalate), adipic acid esters (e.g., diisodecyl adipate and dioctyl adipate), phosphoric acid esters (e.g., triethyl phosphate, tributyl phosphate, trioctyl phosphate and triphenyl phosphate); organic solvents such as toluene, xylene, mesitylene, alkylnaphthalenes, methyl acetate, ethyl acetate and butyl acetate; animal oils; vegetable oils and mineral oils.

Organic solvent-soluble polymers which are used for the preparation of the minute particles such as described above include cellulose diacetate, cellulose triacetate, cellulose acetate propionate, ethyl cellulose, methyl methacrylate, polystyrene and polycarbonate of disphenol A.

In this case, the organic solvent forms a solution, the reagent is dissolved or dispersed in the resulting solution, the solution or dispersion so obtained is added to an aqueous solution of a hydrophilic binder and emulsified or dispersed, and then a part or all of the organic solvent and water are removed by evaporation whereby there can be formed the reagent layer wherein the fine particles containing therein the reagent are dispersed in the hydrophilic binder. Further, microcapsules containing therein the reagent prepared by the same method as described in Japanese Patent Application (OPI) No. 13320/74 (corresponding to U.S. Pat. No. 3,951,851) can also be used as the fine particles.

The thickness of the reagent layer is from about 0.5 μm to about 50 μm and preferably from about 1 μm to about 30 μm.

The size of the hydrophobic fine particles containing the reagent is from about 0.01 μm to about 20 μm and preferably from about 0.1 μm to about 10 μm. Each particle contains the major portion of the reagent in the inner portion thereof, exposing substantially no reagents on the surface thereof and does not allow water to permeate therein.

The amount of the hydrophobic fine particles containing the reagent is from about 3% to about 90% and preferably about 5% to about 80% based on the total weight of the reagent layer.

Hydrophilic binders for use in the reagent layer include water-soluble proteins such as gelatin, albumin and collagen; vegetable gums such as agar, sodium alginate and agarose; and water-soluble synthetic polymers such as an olefin-maleic anhydride copolymer, polyvinyl alcohol, polyvinyl pyrrolidone, polyacrylamide and poly(sodium benzenesulfonate). These binders are able to form a film containing the reagent and the dry film so formed readily allows an aqueous solution containing a component to be determined (aqueous liquid sample) to permeate therein. Of course, in the hydrophilic binder can be incorporated, in addition to the reagent incorporated in the hydrophobic fine particles, a reagent which reacts with the component to be determined, e.g., urease.

With respect to the spreading layer of the chemical analytical material, in addition to the nonfibrous isotropically porous materials described in the patent specifications and references as illustrated hereinbefore, those fabrics which are made hydrophilic can be used as the aqueous liquid sample-spreading layer of the present multi-layer chemical analytical material.

Examples of such nonfibrous isotropically porous materials are those wherein fine porous particles of a brush polymer (generally called a membrane filter), diatomaceous earth or fine crystalline materials (e.g., fine crystalline cellulose) are uniformly dispersed in the binder; porous materials wherein fine spherical beads of glass or a synthetic polymer are brought in point contact with each other and held there with a binder; and a brush polymer in which fine powders of $TiO_2$, $BaSO_4$ or the like are uniformly dispersed. (See James Flinn ed., *Membrane Science and Technology*, Plenun Press, New York (1970); P. Grabar & J. A. de Loureiro, *Annales de L'institut Pasteur*, 65, 159–189 (1939); and U.S. Pat. Nos. 3,129,159 and 1,421,341.)

Examples of such fabrics which are made hydrophilic are a fabric which is degreased by fully washing with water and then dried; and a fabric which is degreased by fully washing with water and then impregnated with a small amount of a hydrophilic polymer, a surfactant, a wetting agent, or a hydrophilic polymer having $TiO_2$ or $BaSO_4$ fine powders dispersed therein. The use of such a hydrophilic fabric as the aqueous liquid sample-spreading layer and the details of such fabrics are described in Japanese Patent Application No. 72047/79, filed June 8, 1979 (corresponding to U.S. Pat. No. 4,292,272.

Where the aqueous liquid sample-spreading layer is made up of the nonfibrous isotropically porous material, its thickness is from about 50 $\mu$m to about 500 $\mu$m, preferably from about 80 $\mu$m to about 300 $\mu$m. In the case of the fabric to be made hydrophilic, the thickness of the fabric which has been made hydrophilic and allowed to dry is from about 80 $\mu$m to about 1 mm, preferably from about 100 $\mu$m to about 400 $\mu$m.

The aqueous liquid sample-spreading layer made up of the nonfibrous isotropically porous material can be made as described in Japanese Patent Application (OPI) Nos. 53888/74 (corresponding to U.S. Pat. No. 3,992,158), 137192/75 (corresponding to U.S. Pat. No. 3,983,005), etc. For example, a solution or dispersion capable of forming a nonfibrous isotropically porous layer is coated on a reagent layer and dried, or a thin layer of the nonfibrous isotropically porous material is bonded to the reagent layer. In the case of the aqueous liquid sample-spreading layer made up of the fabric which has been made hydrophilic, the fabric can be bonded with the reagent layer.

For bonding the nonfibrous isotropically porous material or the fabric which has been made hydrophilic onto the reagent layer, there can be employed a method in which while the reagent layer is wet or after wetting the dry surface of the reagent layer with water or water containing surfactant, the nonfibrous isotropically porous material or the fabric which has been made hydrophilic is brought in close contact with the reagent layer and bonded, if desired, by applying an appropriate pressure, by utilizing the characteristics of the hydrophilic binder polymer contained in the reagent layer. Another method utilizes an adhesive which is permeable in the aqueous liquid sample. In accordance with another method, an adhesive layer permeable in the aqueous liquid sample is provided on the reagent layer.

On the multi-layer chemical analytical material of this invention can be provided, as neccessary, a second reagent layer (see U.S. Pat. No. 3,992,158), a detecting layer (see U.S. Pat. No. 4,042,335) and a barrier layer (see U.S. Pat. Nos. 3,983,005 and 4,066,403). These layers are described in detail in the patent specifications as described hereinbefore. Referring to these descriptions they can be provided in this invention.

In the multi-layer chemical analytical material of this invention, a radiation-blocking layer or a light reflection layer can be provided between the reagent layer and the aqueous liquid sample-spreading layer. Additionally, between the aqueous liquid sample-spreading layer and the reagent layer or the radiation-blocking layer or the light reflection layer can be provided an adhesive layer for which the aqueous liquid sample is permeable, for the purpose of firmly bonding the aqueous liquid sample-spreading layer. The radiation-blocking layer or light reflection layer and adhesive layer are described in detail in the patent specifications as described hereinbefore (e.g., U.S. Pat. Nos. 3,992,158 and 4,042,335). Referring to these descriptions they can be provided in this invention.

As the radiation-blocking layer or light reflection layer, a layer made up of a hydrophilic binder polymer and a fine white powder, such as a $TiO_2$ fine powder and a $BaSO_4$ fine powder, dispersed therein and having a thickness of from about 1 $\mu$m to about 50 $\mu$m, preferably from about 2 $\mu$m to about 20 $\mu$m; a layer made up of a hydrophilic binder polymer and a fine powder of a material having a white or pale metal luster, such as aluminum, dispersed therein and having a thickness of from about 2 $\mu$m to about 50 $\mu$m, preferably from about 2 $\mu$m to about 20 $\mu$m; or an aqueous liquid sample-permeable porous metal thin layer made up of a white or pale metal, such as aluminum, and having a thickness of from about 5 nm to about 100 nm, preferably from about 5 nm to about 50 nm can be provided.

As the adhesive layer, a layer made up of the same polymer as the aqueous liquid sample-permeable hydrophilic polymer used as a binder in the reagent layer, radiation-blocking layer or light reflection layer and having a thickness of from about 0.5 $\mu$m to about 10 $\mu$m, preferably from about 0.7 $\mu$m to about 5 $\mu$m can be used.

In bonding the aqueous liquid sample-spreading layer on the adhesive layer composed of the hydrophilic polymer, the aqueous solution of the hydrophilic polymer is coated on the reagent layer, radiation-blocking layer or light reflection layer and then while it is still wet or after it is dried, the surface is wetted with water or water containing a surfactant, the nonfibrous isotropically porous material or the fabric which has been made hydrophilic is brought into contact with the surface of the adhesive layer and bonded by applying an appropriate pressure. Alternatively, a solution or dispersion capable of forming a nonfibrous isotropically porous layer may be coated on the adhesive layer to obtain the multi-layer chemical analytical material wherein the aqueous liquid sample-spreading layer is firmly bonded.

Hereinafter the multi-layer chemical analytical material of this invention and the hitherto known multi-layer analytical sheet will be compared with reference to the accompanying drawings.

FIG. 1 is an illustrative view of a conventional multi-layer analytical sheet for use in the quantitative determination of the amount of urea in serum wherein an ammonia gas-permeable and water-impermeable hydrophobic second reagent layer 22 composed of a hydrophobic binder and an indicator contained therein, the indicator undergoing discoloration by the action of ammonia gas is provided on a water-impermeable transparent support 1, and a hydrophilic first reagent layer 21 composed of gelatin and urease and a buffering agent dispersed therein is provided on the hydrophobic second reagent layer 22, and furthermore a nonfibrous isotropically porous spreading layer 3 for spreading an aqueous liquid sample is provided on the first reagent layer 21.

On attaching a droplet of serum on the spreading layer 3 from the direction of A, the serum uniformly extends so that the volume per unit area is nearly uniform and reaches the first reagent layer 21 where the urea is decomposed by urease. The ammonia so formed is gasified and permeates the second reagent layer 22 where the pH indicator undergoes discoloration depending upon the amount of ammonia. The degree of discoloration is examined from the direction of B and the amount of urea is quantitatively determined.

Figure 2:
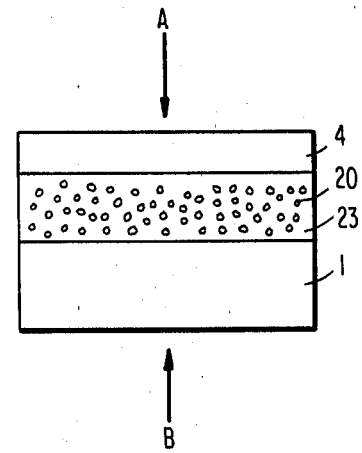
FIG. 2 is an illustrative cross sectional view of an embodiment of the multi-layer chemical analytical material of this invention.

FIG. 2 is an illustrative view of an embodiment of the multi-layer analytical material of this invention wherein a single reagent layer 23 composed of a hydrophilic binder and hydrophobic fine particles 20 dispersed therein is provided on a light-transmitting and water-impermeable support 1, and porous spreading layer 4 is provided on the reagent layer 23. In more detail, a hydrophobic oil or hydrophobic binder containing the indicator is emulsified and dispersed in a hydrophilic binder aqueous solution containing an enzyme system to give a dispersion and the dispersion so prepared is coated to provide the reagent layer 23. The determination of urea in serum is carried out in the same manner as explained for the conventional one of FIG. 1.

From the above comparison, it can be seen that the multi-layer analytical material of this invention is advantageous in its ease of production in comparison with the conventional analytical sheet.

The following examples are given to illustrate this invention in greater detail.

COMPARATIVE EXAMPLE

Multi-Layer Chemical Analytical Material for Analysis of Urea Aqueous Solution

In 6 g of dibutyl phthalate was dissolved 20 mg of a pH indicator, bromothymol blue, to prepare a hydrophobic reagent solution. Then, 20 mg of urease and 200 mg of disodium ethylenediaminetetraacetate (EDTA 2Na) were dissolved in 15 g of a 10% by weight aqueous solution of gelatin to prepare a hydrophilic reagent solution.

The hydrophobic reagent solution was emulsified and dispersed in the hydrophilic reagent solution by a conventional method using a supersonic emulsifier to form an oil-in-water (O/W) type emulsion. The size of the hydrophobic particles containing the bromothymol blue was 5 μm or less.

The dispersion thus obtained was coated on a 170 μm thick transparent polyethylene terephthalate (PET) film which had been undercoated to form a reagent layer. The thickness of the layer after drying was about 20 μm, and microscopic analysis confirmed that the reagent layer was made up of fine oil particles dispersed in the gelatin phase.

After wetting the surface of the reagent layer with water, a membrane filter (Microfilter FM 500 produced by Fuji Photo Film Co., Ltd.) was laminated on and bonded together with the reagent layer by pressing under humid conditions to provide thereon a porous spreading layer. A multi-layer chemical analytical material for the quantitative determination of an urea aqueous solution was thus obtained.

After 10 μl of an urea aqueous solution was dropped on the spreading layer and then heated at 37° C. for 5 minutes, the optical density (OD) was measured with light having a wavelength of 600 nm by use of a reflection optical densitometer. At concentrations of the urea aqueous solution of 30 mg/dl, 60 mg/dl and 100 mg/dl, the corresponding OD values were respectively 0.35, 0.53 and 0.78.

The calibration curve obtained from the above values is nearly a straight line. Therefore, it can be seen that the urea content of an urea aqueous solution can be quantitatively determined by use of the multi-layer chemical analytical material as obtained above.

EXAMPLE 1

Multi-Layer Chemical Analytical Material for Quantitative Analysis of Serum Urea 20 mg of bromothymol blue and 200 mg of ethyl cellulose (a product of Hercules Inc.) were dissolved in a mixed solvent of 6 ml of methyl acetate and 2 ml of dibutyl phthalate to prepare a hydrophobic reagent-polymer solution. Then, 20 mg of urease and 200 mg of EDTA 2Na were dissolved in 15 g of a 10% by weight aqueous solution of gelatin to prepare a hydrophilic reagent-binder aqueous solution.

The hydrophobic reagent-polymer solution was added to the hydrophilic reagent-binder aqueous solution, and the hydrophobic reagent-polymer solution was emulsified and dispersed in the hydrophilic-binder aqueous solution by a conventional method using a supersonic emulsifier. The dispersion was stirred for 30 minutes at 55° C. whereby the organic solvent (methyl acetate) was evaporated off to prepare a dispersion having solid particles of ethyl cellulose (polymer) containing bromothymol blue (pH indicator) dispersed in the hydrophilic reagent-binder aqueous solution. The size of the solid particles of the polymer containing bromothymol blue was about 5 μm or less.

The dispersion thus obtained was coated on a 170 μm thick transparent PET film which has been undercoated with gelatin, and then dried to form a reagent layer in which the solid fine particles of the polymer were dispersed. The thickness of the reagent layer after drying was about 20 μm, and microscopic analysis confirmed that the reagent layer was made up of the solid fine particles of the polymer dispersed in gelatin.

After wetting the surface of the reagent layer with water, a membrane filter (Microfilter FM 500 produced by Fuji Photo Film Co., Ltd.) was laminated on and bonded together with the reagent layer by pressing under humid conditions to provide thereon a porous spreading layer. A multi-layer chemical analytical material for the quantitative determination of serum urea was thus obtained.

Each of buffer aqueous solutions having different pH values ranging between 6 and 8 was applied onto the porous spreading layer of the thus obtained multi-layer chemical analytical material, and then allowed to stand at 37° C. for 5 minutes. No color change of the pH indicator in the reagent layer of each analytical material was observed. This indicates that the solid fine particles of the polymer containing the pH indicator in the multi-layer chemical analytical material were water-impermeable and that the pH indicator (bromothymol blue) was not present in a substantially exposed state on the surfaces of the solid fine particles of the polymer.

10 μl of each of synthetic serums containing urea having different concentrations in a phosphorous acid buffer aqueous solution having a pH value of 7.0 was measured out by means of a micro pipette, and applied onto the porous spreading layer of the multi-layer chemical analytical material, followed by allowing the material to stand at 37° C. for 5 minutes. The optical density (OD) was measured with light having a wavelength of 600 nm by use of a reflection optical densitometer. At concentrations of the urea in the synthetic serum of 30 mg/dl, 60 mg/dl and 100 mg/dl, the corresponding OD values were respectively 0.38, 0.57 and 0.83.

The calibration curve obtained from the above values is nearly a straight line. Therefore, it can be seen that the urea content in the serum can be quantitatively determined by use of the multi-layer chemical analytical material as obtained above.

EXAMPLE 2

Multi-Layer Chemical Analytical Material for Analysis of Ammonia Water

A mixture of 5 mg of 4-(2,4-dinitrobenzyl)-1-propylquinolium chlorate (indicator) and 200 mg of ethyl cellulose (N-100 produced by Hercules Co.) was dissolved in a mixed solvent of 5 ml of ethyl acetate and 3 ml of toluene to prepare a hydrophobic reagent solution. As a hydrophilic binder solution, 20 g of a 10% by weight aqueous solution of gelatin was prepared. The hydrophobic reagent solution was emulsified and dispersed in the hydrophilic reagent solution by a conventional method and by continuing the stirring at 50° C. for 30 minutes, the solvents (ethyl acetate and toluene) were evaporated to produce a dispersion wherein microcapsules in which hydrophobic solid particles containing the indicator were encapsulated with a thin film of ethyl cellulose were dispersed in the hydrophilic binder (gelatin) aqueous solution.

The thus obtained solution was coated on a transparent PET film and dried in the same manner as in Example 1, and subsequently the same porous spreading layer as described in Example 1 was laminated thereon to provide a multi-layer chemical analytical material.

Then, each of buffer aqueous solutions having different pH values ranging between 6 and 8 was applied onto the porous spreading layer of the thus obtained multi-layer chemical analytical material. No color change of the pH indicator was observed. This indicates that the hydrophobic fine particles (microcapsules) containing the pH indicator in the multi-layer chemical analytical material were water-impermeable.

By using ammonia water having different concentrations of 0.02%, 0.04%, 0.08% and 0.10%, the quantitative property was confirmed.

EXAMPLE 3

Multi-Layer Chemical Analytical Material for Quantitative Determination of Serum Urea A solution of 20 mg of bromothymol blue and 200 mg of polystyrene (Sebian A produced by Daicel Ltd.) in a mixed solvent of 5 g of toluene and 3 g of dibutyl phthalate was emulsified and dispersed in 20 g of a 10% by weight aqueous solution of gelatin. Then, by continuing the stirring at 50° C. for 30 minutes, the toluene was evaporated to produce a dispersion wherein microcapsules in which hydrophobic liquid particles containing the indicator were encapsulated with a thin film of polystyrene were dispersed in the hydrophilic binder (gelatin) aqueous solution. To this solution was further added a solution prepared by dissolving 20 mg of urease and 200 mg EDTA 2Na in 2 ml of water. The resulting solution was coated on a transparent PET film and dried in the same manner as in Example 1 to provide an about 15 μm thick reagent layer containing hydrophobic fine particles (microcapsules) which contained the reagent.

On the reagent layer was coated a 5% aqueous solution of gelatin containing 35% of fine titanium dioxide particles to provide thereon a 17 μm thick radiation-blocking layer. Furthermore, on the radiation-blocking layer was laminated the same porous spreading layer as in Example 1 to provide a multi-layer chemical analytical material.

On applying buffer aqueous solutions having different pH values ranging between 6 and 8 onto the multi-layer analytical material as produced above, no color change of the indicator was observed. This indicates that the hydrophobic fine particles containing the reagent were water-impermeable.

Synthetic serums with different concentrations of urea were prepared by adding urea to a phosphoric acid buffer aqueous solution containing 7% of serum protein and having a pH value of 7.0. These serums were tested on the multi-layer chemical analytical material as obtained above, in the same manner as in Example 1. The results are shown in the table below.

| Urea (mg/dl) | Reflection Optical Density (wavelength 600 nm) |
| --- | --- |
| 0 | 0.21 |
| 25 | 0.39 |
| 50 | 0.55 |
| 75 | 0.74 |
| 100 | 0.92 |

The above results indicate that the urea content of the synthetic serum and the reflection optical density vary nearly linearly. It, therefore, can be seen that the multi-layer chemical analytical material permits the quantitative determination of the urea content of aqueous liquid samples containing urea.

EXAMPLE 4

Multi-Layer Chemical Analytical Material for Quantitative Analysis of Blood Urea One surface of a broadcloth (a product of Nisshin Spinning Co., Ltd.) woven at a No. 60 cotton count yarn was made hydrophilic by impregnating it with a 1% aqueous solution of gelatin to prepare a fabric having a gelatin content of about 2.5% at drying. Separately, a reagent layer and a radiation-blocking layer were provided on a transparent PET film and dried in the same manners as those employed in Example 1 and Example 3, respectively. Thereafter, the radiation-blocking layer was wetted and swollen with a 0.2% aqueous solution of a nonionic surface active agent (polyoxyethylene isooctylphenyl ether), and the above-described fabric which had been made hydrophilic was laminated on and bonded together with the thus treated radiation-blocking layer by lightly pressing in such a manner that the surface of the fabric which had been impregnated with the gelatin aqueous solution was brought into contact with the radiation-blocking layer. In this respect, the fabric which had been made hydrophilic functions as the spreading layer for the quantitative determination of an aqueous liquid sample.

Quantitative determination of blood urea could be made in the same manner as in Example 1 using fresh blood (whole blood) by the use of the thus prepared multi-layer chemical analytical material for the quantitiative analysis of blood urea.

EXAMPLE 5

Multi-Layer Chemical Analytical Material for Analysis of Ammonia Water

The same procedure as in Example 2 were repeated except that the cotton fabric prepared in the same manner as in Example 4 was used in place of the membrane filter and laminated on the radiation-blocking layer in the same manner as in Example 4, whereby a multi-layer chemical analytical material was prepared.

By applying 10 $\mu$l of ammonia water having different concentrations of 0.02%, 0.04%, 0.08% and 0.10% onto the porous spreading layer (cotton fabric having been made hydrophilic) of the multi-layer chemical analytical material, the quantitative property was confirmed.

EXAMPLE 6

Multi-Layer Chemical Analytical Material for Quantitative Determination of Serum Urea The same procedures as in Example 3 were repeated except that the cotton fabric prepared in the same manner as in Example 4 was used in place of the membrane filter and laminated on the radiation-blocking layer in the same manner as in Example 4, whereby a multi-layer chemical analytical material was prepared.

The test was carried out in the same manner as in Example 3 using buffer aqueous solutions having different pH values ranging between 6 and 8 and synthetic serums whereby the same results as in Example 3 were obtained.

While the invention has been described in detail and with reference to specific embodiments thereof, it will be apparent to one skilled in the art that various changes and modifications can be made therein without departing from the spirit and scope thereof.

What is claimed is:

1. A multi-layer chemical analytical material comprising
    a light-transmitting and water-impermeable support,
    a reagent layer on the support and
    an aqueous liquid sample-spreading layer on the reagent layer,
wherein the reagent layer is composed of a hydrophilic binder having hydrophobic fine particles dispersed therein, said particles being water impermeable containing a reagent capable of directly or indirectly reacting with a component to be determined to provide a color change and wherein there is substantially no exposure of the reagent on the surface of said hydrophobic fine particles.

2. The material as claimed in claim 1 wherein the hydrophilic binder contains a second reagent capable of reacting with the component to be determined.

3. The material as claimed in claim 1 or 2 wherein said hydrophobic fine particles are oily minute particles prepared by adding a lipophilic binder polymer to an oily matter prepared by dissolving the reagent in an organic solvent substantially incompatible with water.

4. The material as claimed in claim 1 or 2 wherein said hydrophobic fine particles are oily minute particles prepared by dissolving in an organic solvent substantially incompatible with water, a polymer soluble in an organic solvent, and dissolving or dispersing the reagent in the resulting solution.

5. The material as claimed in claim 3 wherein said hydrophobic fine particles are microcapsules prepared by encapsulating said oily minute particles with a thin layer of a lipophilic polymer or a hydrophilic polymer.

6. The material as claimed in claim 1 or 2 wherein said spreading layer is a nonfibrous isotropically porous material.

7. The material as claimed in claim 1 or 2 wherein said spreading layer is a fabric having been made hydrophilic.

8. The material claimed in claim 1 or 2 wherein said reagent dispersed in said hydrophobic fine particles is a reagent to detect urea.

9. The material as claimed in claim 1 or 2 wherein the hydrophilic binder in said reagent layer is selected from the group consisting of water-soluble proteins, vegetable gums, and water-soluble synthetic polymers.

10. The material as claimed in claim 1 or 2 wherein said reagent layer is about 0.5 $\mu$m to about 50 $\mu$m thick.

11. The material as claimed in claim 1 or 2 wherein said hydrophobic fine particles are minute particles prepared by pulverizing a solid polymer containing the reagent.

12. The material as claimed in claim 11 wherein said hydrophobic fine particles are minute particles with a thin layer of a hydrophilic polymer or a hydrophobic polymer.

* * * * *